US005733248A

United States Patent [19]

Adams et al.

[11] Patent Number: 5,733,248

[45] Date of Patent: Mar. 31, 1998

[54] UNIVERSAL GUIDE CATHETER

[75] Inventors: Daniel O. Adams, Orono; Peter T. Keith, St. Paul; David A. VandenEinde, Moundsview; Timothy M. Stivland, Plymouth, all of Minn.

[73] Assignee: SciMed Life Systems, Inc., Maple Grove, Minn.

[21] Appl. No.: 564,819

[22] Filed: Nov. 29, 1995

[51] Int. Cl.$^{6}$ .......... A61M 29/00

[52] U.S. Cl. .......... 600/585; 604/280

[58] Field of Search .......... 128/657, 772; 604/164, 170, 176, 280, 282, 95

[56] References Cited

U.S. PATENT DOCUMENTS

| | | | |
|---|---|---|---|
| 3,867,945 | 2/1975 | Long | 128/349 R |
| 4,033,331 | 7/1977 | Guss et al. | 128/2 M |
| 4,463,779 | 8/1984 | Wink et al. | 138/125 |
| 4,738,666 | 4/1988 | Fuqua | 604/280 |
| 4,759,748 | 7/1988 | Reed | 604/95 |
| 4,822,345 | 4/1989 | Danforth | 604/282 |
| 4,935,017 | 6/1990 | Sylvanowicz | 604/280 |
| 5,030,204 | 7/1991 | Badger et al. | 604/95 |
| 5,098,412 | 3/1992 | Shiu | 604/280 |
| 5,114,402 | 5/1992 | McCoy | 604/95 |
| 5,120,323 | 6/1992 | Shockey et al. | 604/282 |
| 5,163,912 | 11/1992 | Gay et al. | 604/164 |
| 5,167,645 | 12/1992 | Castillo | 604/272 |
| 5,234,407 | 8/1993 | Teirstein et al. | 604/53 |
| 5,254,088 | 10/1993 | Lundquist et al. | 604/95 |
| 5,267,982 | 12/1993 | Sylvanowicz | 604/281 |
| 5,290,229 | 3/1994 | Paskar | 604/95 |
| 5,306,263 | 4/1994 | Voda | 604/281 |
| 5,333,609 | 8/1994 | Bedingham et al. | 128/632 |
| 5,334,168 | 8/1994 | Hemmer | 604/281 |
| 5,372,587 | 12/1994 | Hammerslag et al. | 604/95 |
| 5,383,923 | 1/1995 | Webster, Jr. | 607/125 |
| 5,389,090 | 2/1995 | Fischell et al. | 604/280 |

FOREIGN PATENT DOCUMENTS

| | | |
|---|---|---|
| 0 277 366 A1 | 8/1988 | European Pat. Off. . |

*Primary Examiner*—Sam Rimell
*Attorney, Agent, or Firm*—Nawrocki, Rooney & Sivertson, P.A.

[57] ABSTRACT

Guide catheter incorporating a braidless construction having increased performance characteristics for catheterization procedures. The guide catheter may be universally usable in most anatomical situations with the use of a shaping mandrel. The shape of the guide catheter may be changed during a catheter procedure without removal of the guide catheter from the patient's vascular system.

21 Claims, 3 Drawing Sheets

20 22 36 26 2 2 28 30 24 46

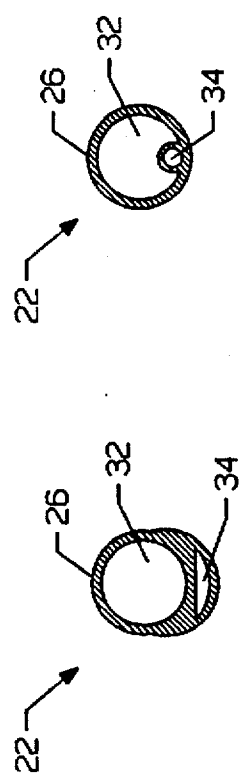
22
26
32
34
FIG. 3
22
26
32
34
FIG. 2
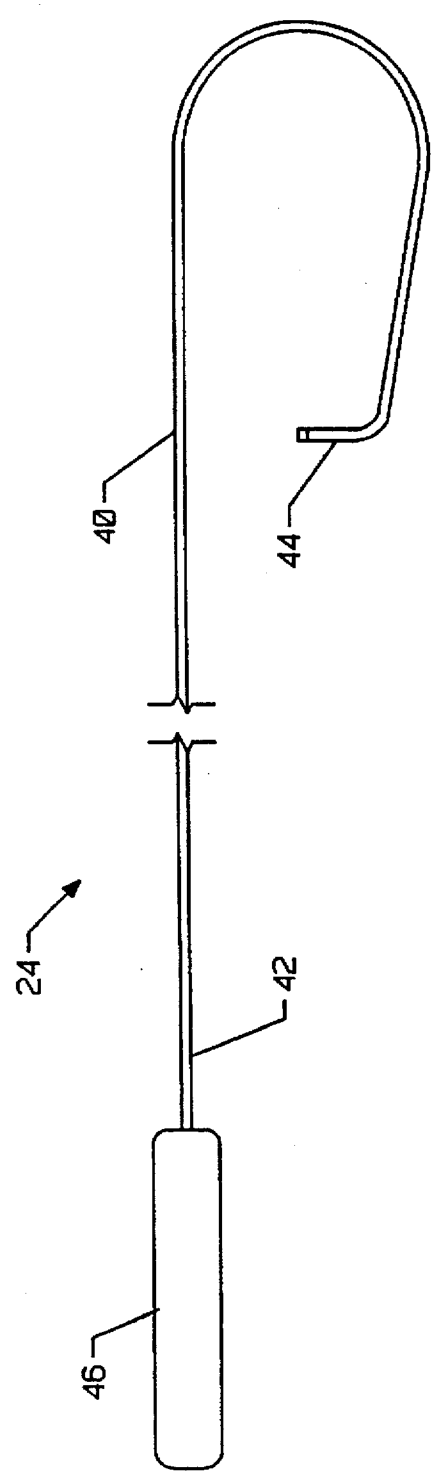
40
44
24
42
46
FIG. 4

UNIVERSAL GUIDE CATHETER

FIELD OF THE INVENTION

The present invention relates to guide catheters and diagnostic catheters used in medical catheterization procedures. In particular, the present invention relates to an improved guide or diagnostic catheter having a simple, braided or braidless catheter design, which is capable of performing the functions of conventional diagnostic and guide catheters. The catheter of the present invention may be universally useable for most anatomical situations.

DESCRIPTION OF THE PRIOR ART

Guide catheters and diagnostic catheters are well known for use in coronary catheterization and percutaneous transluminal coronary angioplasty (PTCA) procedures. Guide catheters aid in treatment of arterial lesions by providing a conduit for positioning dilatation balloon systems across an arterial stenosis. Guide catheters and diagnostic catheters work with various assemblies for performing other medical, therapeutic, and diagnostic procedures, such as dye delivery, arterial flushing, or arterial pressure monitoring.

Diagnostic catheters are used during cardiac catheterization for diagnosis of coronary artery disease in order to define vessel anatomy, isolate lesions, and identify adjacent cardiac branches which may impinge on the lesion and affect ventricular function.

For diagnosis of the coronary artery, the femoral artery is entered percutaneously and a sheath is inserted into the artery to provide access to the patient's vascular system. The diagnostic catheter is inserted into the femoral artery through this introducer sheath over a guide wire and advanced up the aorta to the aortic arch. Once over the aortic arch, the guide wire may be removed. A Y-adapter and manifold assembly are attached to the diagnostic catheter for implementation of diagnostic procedures, such as dye delivery, flushing capabilities, and arterial pressure monitoring.

The diagnostic catheter design generally includes a shaft having a proximal and a distal end. The shaft may be shaped or curved. For example, the shaft may be of a "pigtail" shape. A lumen extends longitudinally through the shaft from the proximal to the distal end. Operably connected to the proximal end of the shaft is a hub assembly, for connection to catheterization equipment, and connected to the distal end of the shaft is a soft tip.

The distal end of the diagnostic catheter shaft is shaped to access the ostium of the coronary artery having the stenotic lesion. Different shapes may be employed for access to the ostium of a right or left coronary artery, mammary artery or the ostium of a bi-pass vein. During the diagnosis procedure, the physician advances and maneuvers the diagnostic catheter shaft within the artery, while at the same time injecting dye. The physician observes the dye using an angiography monitor for visualization of the patient's coronary system.

The diagnostic catheter is advanced and maneuvered until the distal end is properly engaged in the ostium of the coronary artery the physician believes to contain the stenosis. Once seated in the ostium, the physician injects additional dye for observations of obstruction to dye flow, indicative of the coronary disease.

For treatment of the coronary disease through angioplasty or other catheter based treatments, guide catheters are used. The guide catheters provide access to the area within the arterial system containing the stenotic lesion, and support for the treatment catheter which often includes a balloon dilatation system. Guide catheters are similar in construction to diagnostic catheters, although they are generally larger in size. Prior art guide catheters typically have a pre-shaped distal section or tip region to aid in access to the ostium of the coronary artery to receive treatment.

In operation, the guide catheter is introduced over a guide wire through a previously placed femoral introducer sheath and advanced up to the aortic arch. The guide wire can then be removed, and the guide catheter can be advanced and maneuvered until the guide catheter soft tip is properly engaged in the ostium of the coronary artery to be dilatated. A Y-adapter and manifold assembly are attached to the guide catheter hub at the proximal end for implementation of therapeutic procedures, such as dye delivery, flushing capabilities, pressure monitoring and delivery of the dilatation balloon system.

Diagnostic catheters and guide catheters are manufactured in hundreds of shapes and curve styles to accommodate anatomical variances in humans and to access specific areas within the coronary system. Curve shapes are also designed to provide support against the aortic wall when seated within the ostium, to resist the tendency for a catheter to "pop out" of the ostium (termed backout force) when injecting dye or advancing a treatment catheter into the artery. Catheters are presently specifically manufactured with high curve retention to maintain catheter placement within the ostium and to resist backout forces.

During angioplasty procedures, the catheters must be able to traverse pathways through blood vessels to the stenosis in a manner as atraumatic as possible. Therefore, to limit insertion time and discomfort to the patient, the catheter must be stiff enough to resist the formation of kinks, while at the same time the catheter must possess flexibility to be responsive to maneuvering forces when guiding the catheter through the vascular system. It is important that the guide catheter exhibit good torque control such that manipulation of a proximal portion of the guide catheter is responsively translated to the tip or distal end of the catheter to curve and guide the catheter through the tortuous pathways.

To meet the above performance requirements, guide catheters and diagnostic catheters are manufactured using polymers in conjunction with a braid of high-strength fibers or stainless steel wires incorporated into the tube. The guide catheters are generally formed of three layers: a first inner layer commonly formed of polytetrafluoroethylene to decrease the coefficient of friction between a balloon catheter and the guide catheter; a middle layer consisting of braided wire for torque control; and a third, outer layer commonly formed of polyether blocked amide, polyethylene, polyurethane or a nylon-blend for stable positioning of the guide catheter, and providing backout support during other treatment procedures.

During diagnostic and therapeutic procedures, it is often necessary to use more than one shaped or curved catheter to access the right coronary, left coronary, mammary artery, or bypass vein for visualization of each vessel. The procedure of exchanging diagnostic catheters for visualization of different vessels requires more procedural time and exposes the patient to extended x-ray time and fluoroscopy. Additionally, hospitals are required to inventory hundreds of catheters with various curves, tip shapes and diameters to accommodate the various anatomies of each patient.

It is desirable to have a diagnostic or guide catheter design which is universally useable in most anatomical situations, without having to inventory numerous catheter shapes for each catheter size. It is also desirable not to have to switch catheters to access a different coronary artery. It is desirable in catheter design for the inside diameter of the diagnostic or guide catheter to be maximized relative to the outside diameter, providing maximum space for dye flow and dilatation catheter delivery. While designing catheters to meet these design goals, the catheters must continue to meet performance requirements of burst pressure requirements, kink resistance, curve retention, column strength, and torque control for advancement within the patient's vascular system.

SUMMARY OF THE INVENTION

The present invention relates to an improved guide or diagnostic catheter capable of performing the function of conventional diagnostic and guide catheters, which is universally useable in most anatomical situations.

In one preferred embodiment, the catheter of the present invention is for use as a guide or diagnostic catheter in catheter procedures. The catheter includes a generally elongate shaft having a proximal end and a distal end. At least one lumen extends longitudinally between the proximal end and the distal end of the shaft. Means are located within the lumen for providing shape and support to the catheter during the catheter procedure. In one preferred embodiment, the means for providing shape and support is a mandrel having a preformed shape.

The catheter may further include a second lumen extending longitudinally within the catheter shaft from the proximal end to the distal end. The shaft may be formed of a relatively soft polymeric material. The shaft may be formed of a braidless construction. Alternatively, the shaft may be formed of a braided construction.

In one preferred embodiment, the mandrel is responsive to heat for changing between a first, ductile state, and a second, less ductile state. The mandrel may be curved in the second, less ductile state. The second state may be at body temperature.

In one preferred embodiment, the mandrel is formed of shape memory material. The shape memory material may be nitinol or stainless steel.

In yet another embodiment, the present invention includes a method of supporting and shaping a tubular member in a patient's vascular system. The method includes the steps of providing a tubular member having a first lumen and a second lumen. A preshaped mandrel is inserted within the second lumen. The tubular member is advanced over a guide wire which is previously inserted in the patient's vascular system. The method may further include positioning a distal end of the tubular member within the vascular system. The distal end of the tubular member may be positioned within the vascular system by controlling a proximal end of the mandrel. The preshaped mandrel may be inserted within the second lumen after the tubular member is positioned within the patient's vascular system.

The method for supporting and shaping a tubular member in a patient's vascular system may further include removing the mandrel, and resterilizing the mandrel. Alternatively, the mandrel may be removed from the second lumen and a second mandrel having a desired shape may be inserted within the support lumen.

In yet another embodiment, the present invention includes a method of changing the shape of a tubular member located within a patient's vascular system. The method includes withdrawing a mandrel having a first shape from a lumen within the tubular member. A mandrel having a second shape is inserted within the lumen.

In yet another embodiment, the present invention includes a method of changing the state of a tubular member located within a patient's vascular system. The method includes providing a mandrel responsive to a stimulus, within a lumen within the tubular member, wherein the stimulus changes the mandrel between a first state and a second state. In one embodiment, the stimulus is heat. In one embodiment, the first state is a ductile state and the second state is a less ductile state. The mandrel may be formed of shape memory material.

The method may further include flushing the vascular system with a cool flush for inserting the catheter within the vascular system. When the tubular member is in place, the cooling is stopped and the mandrel changes to a second, less ductile state which includes a preset curve. Additionally, the vascular system may be flushed with a cool flush to return the catheter to a ductile state for removing the catheter from the vascular system.

The present invention provides an economically feasible diagnostic or guide catheter design which may be universally usable for most anatomical situations. The catheter of the present invention is less costly to manufacture than conventional catheters, while meeting performance requirements for use, including kink-resistance, curve retention, column strength and torque control.

BRIEF DESCRIPTION OF THE DRAWINGS

The invention will be further described with reference to the accompanying drawings where like numbers refer to like parts in several views and wherein:

FIG. 2 is a cross-sectional view of the guide catheter of FIG. 1.

FIG. 3 is a cross-sectional view of an alternative embodiment of the catheter of FIG. 1.

FIG. 4 is a perspective view showing one embodiment of the shaping mandrel of the catheter invention shown in FIG. 1.

DETAILED DESCRIPTION OF THE PREFERRED EMBODIMENTS

Figure 1:
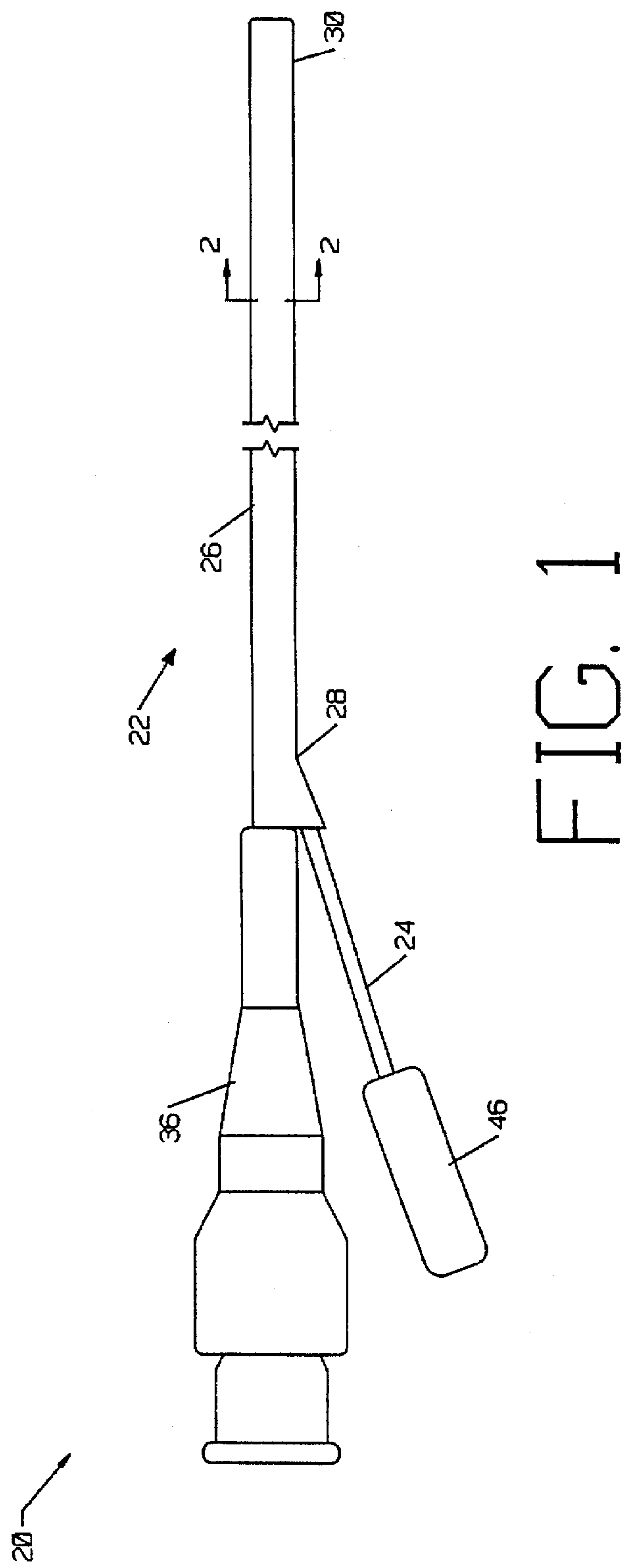
FIG. 1 is a perspective view of a catheter of the present invention having a shaping mandrel disposed therein.

The present invention relates to an improved guide or diagnostic catheter having a simple design, which is capable of performing the functions of conventional diagnostic and guide catheters, while increasing lumen size, backup support, and dye control. The present invention provides an economically feasible diagnostic or guide catheter design which may be universally useable for most anatomical situations.

The catheter of the present invention is less costly to manufacture than conventional catheters, while meeting performance requirements for use, including kink resistance, curve retention, column strength and torque control. Although references throughout this specification may be specifically made to either guide catheters or diagnostic catheters, references made to one are equally applicable to both guide catheters and diagnostic catheters, coronary, neuro, general periphery, and vascular type catheters.

The focus of technology for guide and diagnostic catheters has centered around designs which provide kink resistance, torque response, support, and the largest inside diameter for a given outside diameter within a catheter tubular member. Kink resistance and torque response are necessary so that manipulation of a proximal portion of the catheter is responsively translated to the tip or distal end of the catheter to curve and guide the catheter through the tortuous pathways of a patient's vascular system, to direct and position the distal tip of the catheter near the coronary area receiving treatment while maintaining a open lumen for the treatment procedure.

To achieve these performance characteristics, guide catheter designs have generally included a tubular member formed of three layers, which include braiding or coiling integral to the catheter tube construction. The inner layer can be formed of a polytetrafluoroethylene or lubricous polymer to decrease the coefficient of friction between the balloon catheter or other device and the guide catheter. The middle layer consists of braided or helically wrapped wires or filaments, for torque control. The outer layer is generally a polymeric layer which gives the catheter stable positioning within the patient's vascular system by providing backup support during catheter procedures. The outer layer is typically formed of a polyether block amide, polyethylene, polyurethane, nylon, or a blend of these. Additionally, the outer layer usually is impregnated with a radiopaque material, such as barium sulfate or bismuth subcarbonate, to allow for partial visualization of the catheter shaft during the catheter procedure.

The primary function of the braided middle layer is to provide sufficient torque and kink performance to the catheter body for properly positioning the guide catheter within the coronary anatomy. Once the catheter is positioned within the patient's vascular system, the need for catheter kink and torque performance is no longer necessary.

The present invention provides a catheter (guide or diagnostic) which can be effectively positioned within the patient's coronary anatomy, without utilizing a braided middle layer. The catheter of the present invention includes the use of a shaping mandrel for providing a predetermined shape to the catheter. The shaping mandrel may be removed and exchanged during a catheter procedure without removal of the catheter from the patient's vascular system.

FIG. 1 shows a perspective view of the catheter assembly 20 in accordance with the present invention. The catheter assembly 20 includes a guide catheter 22 positioned over a shaping mandrel 24 (shown straight). The catheter assembly 20 may be universally usable in most anatomical situations. Guide catheter 22 may be a braidless catheter design which maximizes the inside diameter of the guide catheter 22 relative to the outside diameter.

The guide catheter 22 includes a shaft 26 having a proximal end 28 and a distal end 30. Referring to FIG. 2, which is a cross-sectional view of the catheter shaft 26 of FIG. 1, a treatment lumen 32 and support lumen 34 extend longitudinally through the shaft 26 from the proximal end 28 to the distal end 30. Operably connected to the proximal end 28 of the shaft 26 is a hub assembly 36 which communicates with the treatment lumen 32.

Guide catheter 22 is formed of a polymeric material, such as polyether blocked amide, polyethylene, polyurethane or a nylon blend. Additionally, the catheter shaft may be impregnated with a radiopaque material, such as barium sulfate or bismuth subcarbonate, for visualization of the catheter during catheter procedures. A radiopaque marker band may also be placed at the distal end 30. Guide catheter 22 may be clear to allow for inspection of air embolism.

The guide catheter 22 is formed by extrusion of the lumen shaft 26. In a preferred embodiment shown in FIG. 2, the support lumen 34 is "D" shaped and accommodates the insertable shaping mandrel 24, and the treatment lumen 32 is relatively larger and used for dye injection or treatment catheter delivery. Referring to FIG. 3, alternatively it is recognized that the dual lumens may take on various shapes and forms, while performing the functions of the present invention.

In a preferred embodiment, the wall thickness for the guide catheter 22 is in the range of 0.003 inches to 0.009 inches, depending on the material used, but relatively thinner than conventional guide catheter wall thicknesses. Although an inner polytetrafluoroethylene layer may be located within treatment lumen 32, alternatively, a relatively lubricous polymer such as polyethylene may be used to form the catheter shaft. A soft tip may be located at the proximal end 28. Since the guide catheter 22 wall thickness is relatively thin and flexible, a soft tip may not be required.

The guide catheter construction of the present invention provides a universal guide catheter which is easily adaptable to most anatomical situations. The guide catheter 22 design is less costly to manufacture since it is a braidless catheter design, and does not require a soft tip.

Figure 5:
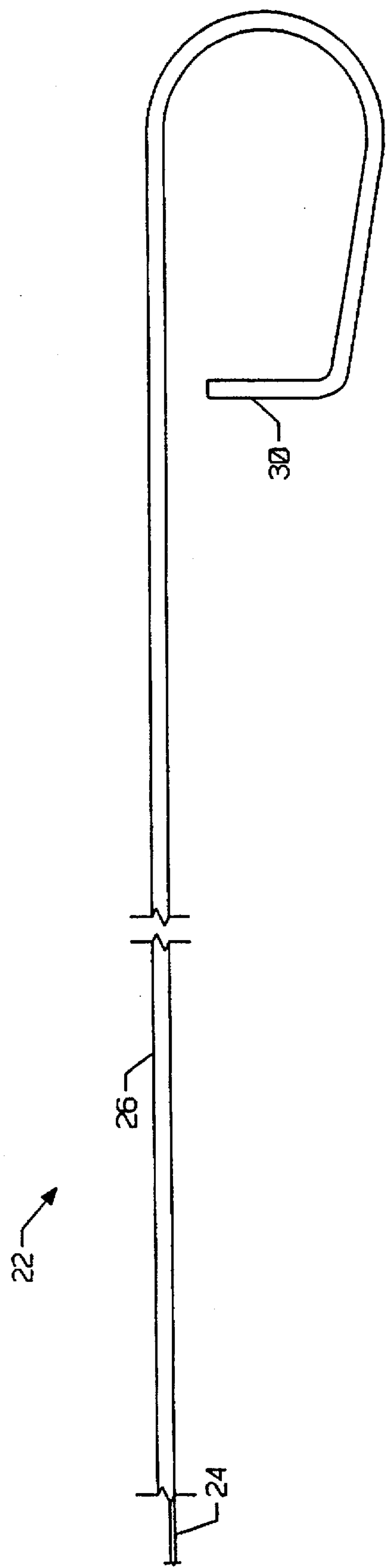
FIG. 5 is a partial perspective view of the catheter of FIG. 1 having the shaping mandrel of FIG. 4 disposed therein.

Shaping mandrel 24 is used for providing shape to the guide catheter 22 and for providing kink-resistance and torquability to the guide catheter 22 when positioning the guide catheter 22 within a patient's vascular system. Referring to FIG. 4, shaping mandrel 24 includes a shaft 40 having a proximal end 42 and a distal end 44. Shaping mandrel 24 is formed of a resilient material, such as stainless steel or nitinol. In a preferred embodiment, shape mandrel 24 is formed of nitinol, and has a length longer than the guide catheter 22. The nitinol may have super elastic properties. Shaping mandrel 24 may be shaped similar to the shapes of conventional guide catheters for accessing specific coronary areas. When inserted into the support lumen 34 of guide catheter 22, guide catheter 22 takes on the shape of shaping mandrel 24 as shown in FIG. 5.

In one preferred embodiment, shaping mandrel 24 has a rectangular cross-section for maximum torquability and bend retention. In one embodiment, the mandrel 24 has a preferred cross-sectional shape of 0.01 inches by 0.030 inches, and fits tightly within the support lumen 34 such that torque transmitted through the proximal end 28 of the shaping mandrel 24 is delivered to the distal end 30 of the guide catheter 22 for positioning of the distal end 30 within the desired ostium.

Due to the shaping mandrel 24 construction, the shaped curves within the shaping mandrel shaft 40 are resilient, and straighten when inserted into the support lumen when the guide catheter 22 is constrained within a straight introducer or the patient's aorta, or when inserted over a guide wire of sufficient stiffness. The shaping mandrels may be reusable by resterilization after use by methods known in the art, such as autoclave sterilization. The curve of the shaping mandrel may also be altered by the physician for a specific anatomy.

Located on the proximal end 42 of shaping mandrel 24 is a handle 46. During positioning of the guide catheter 22, the shaping mandrel 24 handle 46 is located outside the body to facilitate the application of torque and advancement of the guide catheter 22 for positioning the guide catheter 22 within a patient's vascular system. The guide catheter 22 may be deep seated into the ostium of a selected artery by holding onto the handle 46 at the proximal end 42 of the shape mandrel 24 and advancing the guide catheter 22. The guide catheter 22 shape is maintained by shaping mandrel 24, while the soft distal end 44 may be seated within the ostium of the artery receiving treatment. This method provides more balloon catheter support without trauma to the vessel, as with conventional guide catheters.

The guide catheter 22 allows physicians to easily change from one guide catheter shape to another without removing guide catheter 22 from the patient's vascular system. To change shapes to access a different coronary ostium, the shaping mandrel 24 is removed and the catheter 22 is pulled back just into the aorta. A second shaping mandrel 24 having a different curve is inserted into the support lumen 34 of the guide catheter 22. Guide catheter 22 may now be repositioned into the ostium of the next desired artery.

The shaping mandrel 24 may also be changed during a catheterization procedure to add backup support to the guide catheter 22, without removing the treatment catheter from the artery. During this procedure, the presence of the treatment catheter lends additional support to the guide catheter 22 during the exchange of the shape mandrel 24. Procedure time would be reduced, since the physician does not have to remove the treatment catheter and guide catheter and reinsert and reposition the catheters at a later time.

For use in an angioplasty procedure, the patient's femoral artery is entered percutaneously and a sheath is inserted for access to the vascular system. Although the angioplasty procedure described herein utilizing the femoral artery to access the patient's vascular system is the most common method, it is also recognized that the present invention may be used for brachial and radial artery access using similar procedures. The desired shaping mandrel 24 is inserted into the guide catheter 22 support lumen 34. A guide wire, in a preferred embodiment a 0.035 inch guide wire, is inserted through the femoral sheath into the patient's vascular system and up over the aortic arch.

The guide catheter assembly 20 including guide catheter 22 and shaping mandrel 24 is introduced over the guide wire and advanced through the femoral artery and up over the aortic arch. During advancement, the shaping mandrel 24 provides torquability, steerability, and kink-resistance to the guide catheter 22. The catheter assembly 20 is controlled by the handle 46 located on the proximal end 42 of shaping mandrel 24. Alternatively, the shaping mandrel 24 may be inserted after the guide catheter 22 is positioned within the patient's vascular system.

The guide wire can then be removed. A Y-adaptor and a manifold assembly are attached to the guide catheter hub assembly 36 for pressure monitoring, and to deliver contrast dye and flushing, for location of the ostium. Using the control handle 46, the catheter assembly 20 is advanced to deep seat the guide catheter distal end 30 in the ostium of the coronary to receive treatment.

If, during the angioplasty procedure, the physician discovers that a different shaped guide catheter 22 is necessary to complete the procedure, the physician simply removes the shaping mandrel 24 and reinserts a second shaping mandrel having the desired shape using the procedure as previously described. The physician may now proceed with performing the desired angioplasty procedure.

It is also recognized that the shaping mandrel 24 may be formed of a shape memory material. In a preferred embodiment, the shaping mandrel 24 would be formed of shape memory nitinol. The patient's body temperature would be used as the activation temperature for the shape memory shaping mandrel 24.

In a preferred embodiment, the shaping mandrel 24 would have a desired preformed shape. The shaping mandrel 24 would be cooled, such as by the use of a cool saline flush, to change the shaping mandrel into its ductile phase and subsequently, the shaping mandrel would be bent straight. The shaping mandrel 24 would be inserted into the patient within a catheter assembly 20 while continuing to provide a cool saline flush around the shaping mandrel 24.

Once located within the desired area of the patient's body, the cool saline flush may be stopped. Due to the drop in temperature from the absence of the cool flush, the shaping mandrel 24 shape memory would return to its curved, stiff, resilient state. If removal of the shaping mandrel 24 was desired, the shaping mandrel 24 can be formed with a stiffness which would allow it to be simply pulled out, or the shaping mandrel 24 can be cool flushed to return it to its ductile state to facilitate removal.

The guide catheter assembly 20 of the present invention, including guide catheter 22 and shaping mandrel 24, would provide for increased performance during diagnostic procedures. The dimensions of the diagnostic catheter could be scaled appropriately and constructed to withstand adequate burst pressures for high pressure dye delivery typical of diagnostic procedures. The present invention would allow the physician to use diagnostic catheter shapes for visualizing various areas of the coronary system, without having to remove the diagnostic catheter from the patient's body. The time saving procedure using the present invention also results in less patient exposure to fluoroscopy.

The guide catheter assembly of the present invention is universally useful in most anatomical situations, while greatly reducing the amount of catheter inventory required by hospitals. The catheters may be manufactured in a generally straight form for each catheter size, with specific shapes being provided by the resterilizable shaping mandrels.

The catheter assembly of the present invention allows the physician to change the catheter shape for access to a different coronary ostium, without withdrawing the catheter from the patient's vascular system. The catheter assembly of the present invention allows for deep seating of the guide catheter, for enhanced support for positioning of treatment catheters. The catheter can be of a braidless or braided design. The braidless design provides for an inside diameter of the diagnostic or guide catheter which maximized relative to the outside diameter, providing maximum space for dye flow and dilatation catheter delivery.

It will be understood, that this disclosure is, in many respects, only illustrative. Changes may be made in details, particularly in matters of shape, size, material, and arrangement of parts without exceeding the scope of the invention. Accordingly, the scope of the invention is as defined within the language of the appended claims.

What is claimed is:

1. A catheter assembly for use as a guide or diagnostic catheter capable of changing the shape of the guide or diagnostic catheter during a catheter procedure comprising:

a generally elongate shaft having a proximal end and a distal end, having a first lumen extending longitudinally between the proximal end and the distal end;

a shaping mandrel having a preformed shape located within the first lumen to provide shape and support to the catheter during the catheter procedure; and a second lumen extending longitudinally within the catheter shaft from the proximal end to the distal end.

2. The catheter assembly of claim 1, wherein the shaft is formed of a relatively soft polymeric material.

3. The catheter assembly of claim 1, wherein the shaft is braidless.

4. The catheter of claim 1, wherein the shaping mandrel is responsive to heat for changing between a first, ductile state and a second, less ductile state.

5. The catheter of claim 4, wherein the shaping mandrel is curved in the second state.

6. The catheter of claim 4, wherein the second state is at body temperature.

7. The catheter of claim 1, wherein the shaping mandrel is formed of shape memory material.

8. The catheter of claim 1, wherein the shape memory material is Nitinol.

9. A method of supporting and shaping a tubular member in a patient's vascular system comprising the steps of:

providing a tubular member having a first lumen and a second lumen:

inserting a preshaped mandrel within the first lumen to shape and support the tubular member; and advancing the tubular member over a guidewire inserted in the patient's vascular system wherein the guidewire passes through the second lumen.

10. The method of claim 9, further including the step of positioning a distal end of the tubular member within the vascular system.

11. The method of claim 10, wherein the distal end of the tubular member is positioned within the vascular system by controlling a proximal end of the mandrel.

12. The method of claim 10, further comprising the step of removing the mandrel.

13. The method of claim 12, further comprising the step of resterilizing the mandrel.

14. The method of claim 10, further comprising the steps of:

removing the mandrel from the first lumen; and inserting a second mandrel having a desired shape within the first lumen.

15. A method of changing the shape of a tubular member located within a patient's vascular system comprising the steps of:

providing the tubular member with a support lumen and a treatment lumen;

inserting a first mandrel having a first shape within the support lumen to provide a shape to the tubular member which corresponds to the shape of the first mandrel;

withdrawing the first mandrel from the support lumen within the tubular member; and inserting a mandrel having a second shape within the support lumen.

16. A method of changing the state of a tubular member having a support lumen and a treatment lumen located within a patient's vascular system comprising the step of providing a mandrel responsive to a stimulus, within the support lumen within the tubular member, wherein the stimulus changes the mandrel between a first state and a second state.

17. The method of claim 16, wherein the stimulus is heat.

18. A method of changing the state of a tubular member located within a patient's vascular system comprising:

providing a mandrel responsive to a stimulus, within a lumen within the tubular member, wherein the stimulus changes the mandrel between a first state and a second state, wherein the stimulus is heat; and flushing the vascular system for inserting the catheter within the vascular system.

19. A method of changing the state of a tubular member located within a patient's vascular system comprising:

providing a mandrel responsive to a stimulus, within a lumen within the tubular member, wherein the stimulus changes the mandrel between a first state and a second state, wherein the stimulus is heat;

flushing the vascular system with a cool flush; and removing the catheter from the patient's vascular system.

20. The method of claim 18, wherein the first state is a ductile state and the second state is a relatively less ductile state.

21. The method of claim 18, wherein the mandrel is formed of a shape memory material.

* * * * *